United States Patent [19]

Wagner et al.

[11] Patent Number: 4,988,719
[45] Date of Patent: Jan. 29, 1991

[54] 3,7-DISUBSTITUTED BENZOTHIAZOLONES AND FUNGICIDAL USE THEREOF

[75] Inventors: Klaus Wagner, Cologne; Gerd Hänssler, Leverkusen, both of Fed. Rep. of Germany

[73] Assignee: Bayer Aktiengesellschaft, Leverkusen, Fed. Rep. of Germany

[21] Appl. No.: 326,859

[22] Filed: Mar. 21, 1989

[30] Foreign Application Priority Data

Mar. 25, 1988 [DE] Fed. Rep. of Germany ....... 3810077
Oct. 19, 1988 [DE] Fed. Rep. of Germany ....... 3835576

[51] Int. Cl.$^5$ .................... A01N 43/78; C07D 277/70
[52] U.S. Cl. .................................. 514/369; 548/159; 548/171
[58] Field of Search ................. 548/159, 171; 514/369

[56] References Cited

U.S. PATENT DOCUMENTS

| Re. 32,769 | 10/1988 | D'Amico | 546/280 |
| 4,187,097 | 2/1980 | D'Amico | 71/90 |
| 4,227,915 | 10/1980 | D'Amico | 71/90 |

FOREIGN PATENT DOCUMENTS

| 0003075 | 7/1979 | European Pat. Off. |
| 1100372 | 2/1961 | Fed. Rep. of Germany |
| 2101150 | 8/1972 | Fed. Rep. of Germany |

OTHER PUBLICATIONS

Chemische Berichte, vol. 107, No. 1, Jan. 1974, pp. 305–316.

*Primary Examiner*—David B. Springer
*Attorney, Agent, or Firm*—Sprung Horn Kramer & Woods

[57] ABSTRACT

Fungicidally active 3,7-disubstituted benzothiazolones of the formula

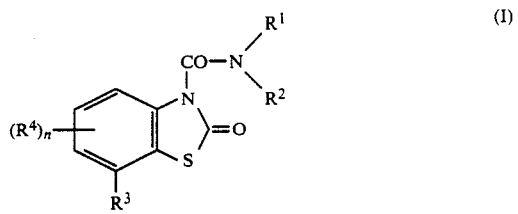

in which
n stands for the numbers 0, 1, 2 or 3,
$R^1$ stands for hydrogen or optionally substituted alkyl,
$R^2$ stands for hydrogen, hydroxyl or for an optionally substituted radical from the group consisting of alkyl, cycloalkyl, cycl;oalkylalkyl, alkenyl, alkinyl, alkoxy, alkenyloxy, aralkoxy, aralkyl, aryl, heterocyclyl and heterocyclylalkyl, or
$R^1$ and $R^2$ together stand for an alkylene chain which is optionaklly substituted and optionally interrupted by hetero atoms,
$R^3$ stands for halogen or alkyl, or, in the event that n stands for 0, may also stand for halogenoalkyl and
$R^4$ stands for halogen, alkyl or halogenoalkyl.

6 Claims, No Drawings

3,7-DISUBSTITUTED BENZOTHIAZOLONES AND FUNGICIDAL USE THEREOF

The present invention relates to new 3,7-disubstituted benzothiazolones, a process for their preparation and their use in pesticides.

It has already been disclosed that cyclic sulphur compounds can be used for combating certain plant diseases Thus, for example, 6-methyl-2,3-quinoxalinedithiol cyclocarbonate (chinomethionat/Morestan) can be used against mildew in fruit-growing (cf. DE-AS (German Published Specification) 1,100,372). However, the action of this known compound is not always satisfactory, in particular when low concentrations of active compound are used.

Furthermore, nitro- and/or trifluoromethyl-substituted benzothiazolones have been disclosed (cf. Chem. Ber. 107 (1974), 305–315; DE-OS (German Published Specification) 2,101,150) which also have a biological action.

New 3,7-disubstituted benzothiazolones of the general formula (I)

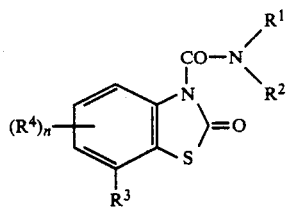

in which
n stands for the numbers 0, 1, 2 or 3,
$R^1$ stands for hydrogen or optionally substituted alkyl,
$R^2$ stands for hydrogen, hydroxyl or for an optionally substituted radical from the series comprising alkyl, cycloalkyl, cycloalkylalkyl, alkenyl, alkinyl, alkoxy, alkenyloxy, aralkoxy, aralkyl, aryl, heterocyclyl or heterocyclylalkyl, or
$R^1$ and $R^2$ together stand for an alkylene chain which is optionally substituted and optionally interrupted by hetero atoms,
$R^3$ stands for halogen or alkyl, or, in the event that n stands for 0, also stands for halogenoalkyl, and
$R^4$ stands for halogen, alkyl or halogenoalkyl, have been found.

Furthermore, it has been found that the new compounds of the general formula (I)

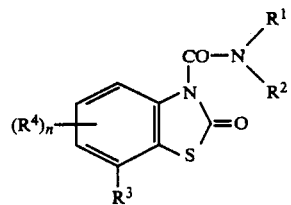

in which
n stands for the numbers 0, 1, 2 or 3,
$R^1$ stands for hydrogen or optionally substituted alkyl,
$R^2$ stands for hydrogen, hydroxyl or for an optionally substituted radical from the series comprising alkyl, cycloalkyl, cycloalkylalkyl, alkenyl, alkinyl, alkoxy, alkenyloxy, aralkoxy, aralkyl, aryl, heterocyclyl or heterocyclylalkyl, or
$R^1$ and $R^2$ together stand for an alkylene chain which is optionally substituted and optionally interrupted by hetero atoms,
$R^3$ stands for halogen or alkyl, or, in the event that n stands for 0, also stands for halogenoalkyl, and
$R^4$ stands for halogen, alkyl or halogenoalkyl,
are obtained when 2,7-disubstituted benzothiazole-3-oxides of the general formula (II)

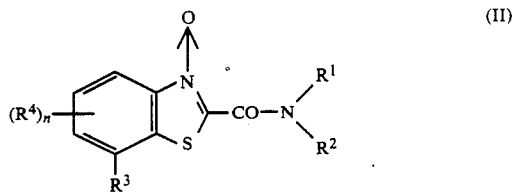

in which
n, $R^1$, $R^2$, $R^3$ and $R^4$ have the abovementioned meanings,
are reacted with phosphoryl chloride (POCl$_3$), if appropriate in the presence of a diluent.

The new 3,7-disubstituted benzothiazolones of the general formula (I) are distinguished by a powerful biological action, in particular a fungicidal action.

Surprisingly, the compounds of the formula (I) according to the invention show, for example, a considerably more powerful fungicidal action that the known fungicide 6-methyl-2,3-quinoxalinedithiol cyclocarbonate.

Formula (I) provides a general definition of the 3,7-disubstituted benzothiazolones according to the invention. Preferred compounds of the formula (I) are those in which
n stands for the numbers 0, 1 or 2,
$R^1$ stands for hydrogen or for straight-chain or branched alkyl which has 1 to 6 carbon atoms and which is optionally substituted once, twice or three times by identical or different substituents from the series comprising halogen, hydroxyl, C$_1$–C$_4$-alkoxy, C$_1$–C$_4$-alkoxy-carbonyl and/or di(C$_1$–C$_4$-alkyl)-amino,
R$_2$ stands for hydrogen, hydroxyl, for straight-chain or branched alkyl which has 1 to 6 carbon atoms and which is optionally substituted once, twice or three times by identical or different substituents from the series comprising halogen, hydroxyl, cyano, benzoyl, C$_1$–C$_4$-alkoxy, C$_1$–C$_4$-alkoxy-carbonyl and/or di-(C$_1$–C$_4$-alkyl)-amino, or stands for cycloalkyl which has 3 to 6 carbon atoms or cycloalkylalkyl which ha$ 3 to 6 carbon atoms in the cycloalkyl moiety and 1 to 3 carbon atoms in the alkyl moiety, which are optionally substituted once, twice or three times by identical or different substituents from the series comprising halogen and/or C$_1$–C$_4$-alkyl, or stands for straight-chain or branched alkenyl which has 3 to 6 carbon atoms and which is optionally substituted once, twice or three times by identical or different substituents from the series comprising halogen, cyano and/or C$_1$–C$_4$-alkoxy-carbonyl, or stands for straight-chain or branched alkinyl which has 3 to 6 carbon atoms and which is optionally substituted once, twice or three times by identical or different substituents from the series comprising halogen, cyano and/or C$_1$–C$_4$-alkoxy-carbonyl, or stands for straight-chain or branched alkoxy which has 1 to 6 carbon atoms and which is optionally substituted once, twice or three times by identical or different substituents from the series comprising halogen, cyano, $C_1$-$C_4$-alkoxy and/or $C_1$-$C_4$-alkoxy-carbonyl, or stands for straight-chain or branched alkenyloxy which has 3 to 6 carbon atoms and which is optionally substituted once, twice or three times by identical or different halogen substituents, or stands for benzyloxy which is optionally substituted once, twice or three times by identical or different substituents from the series comprising halogen, nitro, cyano, $C_1$-$C_4$-alkyl, $C_1$-$C_4$-alkoxy, $C_1$-$C_4$-alkoxy-carbonyl and/or halogenoalkyl having 1 or 2 carbon atoms and 1 to 5 identical or different halogen atoms, or stands for aralkyl which has 6 to 10 carbon atoms in the aryl moiety and 1 to 4 carbon atoms in the straight-chain or branched alkyl moiety, each of the alkyl and aryl moieties optionally being substituted once, twice or three times by identical or different substituents from the series comprising halogen, hydroxyl, phenyl, nitro, cyano, $C_1$-$C_4$-alkyl, $C_1$-$C_4$-alkoxy, $C_1$-$C_4$-alkoxy-carbonyl and/or halogenoalkyl having 1 or 2 carbon atoms and 1 to 5 identical or different halogen atoms, or stands for phenyl or naphthyl, which are optionally substituted once, twice or three times by identical or different substituents from the series comprising halogen, hydroxyl, nitro, cyano, $C_1$-$C_4$-alkyl, halogenoalkyl having 1 or 2 carbon atoms and 1-5 identical or different halogen atoms, $C_1$-$C_4$-alkoxy, $C_1$-$C_2$-halogenoalkoxy, $C_1$-$C_4$-alkylthio, $C_1$-$C_2$-halogenoalkylthio and/or $C_1$-$C_4$-alkoxycarbonyl, or stands for a single-ring heterocyclic radical, double-ring heterocyclic radical, single ring heterocyclylalkyl having 1 to 4 carbon atoms in the alkyl or double-ring heterocyclylalkyl having 1 to 4 carbon atoms in the alkyl, which are optionally substituted once, twice or three times by identical or different substituents from the series comprising halogen, nitro, cyano, $C_1$-$C_4$-alkyl, $C_1$-$C_4$-alkoxy and/or $C_1$-$C_4$-alkoxycarbonyl, heterocyclic radicals which may be mentioned being furyl, thienyl, oxazolyl, thiazolyl, oxadiazolyl, thiadiazolyl, pyridyl, pyrimidinyl, pyrrolidinyl, thiomorpholinyl, morpholinyl,

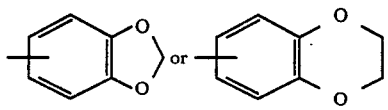

and the corresponding radicals which are linked via alkylene, or $R^1$ and $R^2$ together stand for an alkylene chain which has 2 to 8 ring members and which is optionally substituted once, twice or three times by identical or different $C_1$-$C_4$-alkyl substituents and which is optionally interrupted by one or more than one hetero atoms, such as, for example, oxygen, $R^3$ stands for halogen, methyl or ethyl and, in the event that n stands for 0, also stands for halogenoalkyl which has 1 to 3 carbon atoms and 1 to 6 identical or different halogen atoms, and $R^4$ stands for halogen, methyl, ethyl or halogenoalkyl which has 1 to 3 carbon atoms and 1 to 6 identical or different halogen atoms.

Particularly preferred compounds of the formula (I) are those in which n stands for the numbers 0, 1 or 2, $R^1$ stands for hydrogen or for straight-chain or branched alkyl which has 1 to 4 carbon atoms and which is optionally substituted once or twice by identical or different substituents from the series comprising hydroxyl, $C_1$-$C_2$-alkoxy or $C_1$-$C_2$-alkoxy-carbonyl, $R^2$ stands for straight-chain or branched alkyl which has 1 to 6 carbon atoms and which is optionally substituted once or twice by identical or different substituents from the series comprising hydroxyl, cyano, benzoyl, $C_1$-$C_2$-alkoxy, $C_1$-$C_2$-alkoxy-carbonyl or di-($C_1$-$C_2$-alkyl)-amino, or stands for cycloalkyl which has 3 to 6 carbon atoms, for cycloalkylmethyl or -ethyl which has 3 to 6 carbon atoms in the cycloalkyl moiety, for straight-chain or branched alkenyl which has 3 to 6 carbon atoms, for straight-chain or branched alkinyl which has 3 to 6 carbon atoms, for straight-chain or branched alkoxy which has 1 to 6 carbon atoms, for straight-chain or branched alkenyloxy which h 3 to 6 carbon atoms, or stands for benzyloxy which is optionally substituted once or twice by identical or different substitutents from the series comprising fluorine, chlorine, methyl and/or methoxy, or stands for phenylalkyl which has 1 to 3 carbon atoms in the alkyl moiety and which is optionally substituted once, twice or three times in the phenyl and/or alkyl moiety by identical or different substituents from the series comprising fluorine, chlorine, hydroxyl, phenyl, $C_1$-$C_4$-alkyl, $C_1$-$C_2$-alkoxy, trifluoromethyl, and/or $C_1$-$C_2$-alkoxy-carbonyl, or stands for naphthylmethyl, or stands for phenyl which is optionally substituted once, twice or three times by identical or different substituents from the series comprising fluorine, chlorine, bromine, hydroxyl, $C_1$-$C_4$-alkyl, trifluoromethyl, $C_1$-$C_2$-alkoxy, trifluoromethoxy, $C_1$-$C_2$-alkylthio and/or trifluoromethylthio, stands for furylmethyl, for pyridylmethyl, for morpholinyl which is optionally substituted once or twice by methyl, for morpholinyl-$C_1$-$C_3$-alkyl or for pyrrolidinyl-$C_1$-$C_3$-alkyl which is optionally substituted once or twice by identical or different $C_{1-3}$-alkyl substituents, or stands for

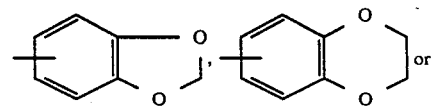

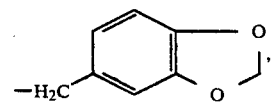

or $R^1$ and $R^2$ together with the nitrogen atom to which they are bonded stand for morpholinyl, piperidinyl or pyrrolidinyl which is optionally substituted once, twice or three times by identical or different substituents from the series comprising methyl and/or ethyl, $R^3$ stands for chlorine or, in the event that n stands for 0, also stands for trifluoromethyl, and $R^4$ stands for chlorine or trifluoromethyl.

Halogen stands for fluorine, chlorine, bromine or iodine, preferably for fluorine, chlorine or bromine, particularly preferably for fluorine or chlorine on its own or in combinations such as halogenoalkyl, unless defined otherwise.

All the radicals which can be substituted are substituted once or more than once by identical or different substituents, preferably once, twice or three times, and particularly preferably once or twice, unless indicated otherwise.

Examples of the compounds of the formula (A) according to the invention are listed in Table 1 below and also in the Preparation Examples.

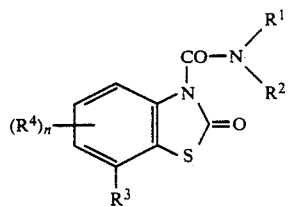

TABLE 1

Examples of the compounds of the formula (I)

| $R^1$ | $R^2$ | $R^3$ | $R^4$ | n |
|---|---|---|---|---|
| H | $CH_3$ | Cl | — | 0 |
| $CH_3$ | $CH_3$ | Cl | — | 0 |
| H | $C_2H_5$ | Cl | — | 0 |
| $C_2H_5$ | $C_2H_5$ | Cl | — | 0 |
| H | $C_3H_7$-n | Cl | — | 0 |
| H | $CH(CH_3)_2$ | Cl | — | 0 |
| H | $C_4H_9$-n | Cl | — | 0 |
| H | $CH_2CH(CH_3)_2$ | Cl | — | 0 |
| H | $CH(C_2H_5)_2$ | Cl | — | 0 |
| H | OH | Cl | — | 0 |
| H | cyclopropyl | Cl | — | 0 |
| H | cyclobutyl | Cl | — | 0 |
| H | cyclopentyl | Cl | — | 0 |
| H | cyclohexyl | Cl | — | 0 |
| H | $-CH_2$-cyclopropyl | Cl | — | 0 |
| H | $-CH_2$-cyclobutyl | Cl | — | 0 |
| H | $-CH_2$-cyclopentyl | Cl | — | 0 |
| H | $-CH_2$-cyclohexyl | Cl | — | 0 |
| H | $-CH_2-CH=CH_2$ | Cl | — | 0 |
| H | $-CH_2-C\equiv CH$ | Cl | — | 0 |
| H | $OCH_3$ | Cl | — | 0 |
| H | $OC_2H_5$ | Cl | — | 0 |
| H | $OC_3H_7$-n | Cl | — | 0 |
| H | $OCH(CH_3)_2$ | Cl | — | 0 |
| H | $OC_4H_9$-n | Cl | — | 0 |
| H | $OCH_2CH(CH_3)_2$ | Cl | — | 0 |
| H | $OCH_2CH=CH_2$ | Cl | — | 0 |

TABLE 1-continued

Examples of the compounds of the formula (I)

| $R^1$ | $R^2$ | $R^3$ | $R^4$ | n |
|---|---|---|---|---|
| H | $-OCH_2-C_6H_5$ | Cl | — | 0 |
| H | $-CH_2-C_6H_5$ | Cl | — | 0 |
| $CH_3$ | $-CH_2-C_6H_5$ | Cl | — | 0 |
| H | $-C_6H_5$ | Cl | — | 0 |
| H | $-C_6H_4-Cl$ (4-) | Cl | — | 0 |
| H | $-CH_2-C_6H_4-Cl$ (4-) | Cl | — | 0 |
| H | $-C_6H_4-Cl$ (2-) | Cl | — | 0 |
| H | $-CH_2-C_6H_4-Cl$ (2-) | Cl | — | 0 |
|  | $-(CH_2)_4-$ | Cl | — | 0 |
|  | $-(CH_2)_5-$ | Cl | — | 0 |
| H | $-CH_2-C_6H_5$ | Cl | (6-)Cl | 1 |
| H | $-CH_2-C_6H_4-F$ (2-) | Cl | — | 0 |
| H | $-CH_2-C_6H_4-F$ (4-) | Cl | — | 0 |

TABLE 1-continued
| R¹ | R² | R³ | R⁴ | n |
|---|---|---|---|---|
| H | 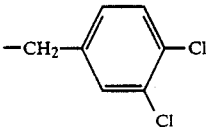 -CH₂-(3,4-dichlorophenyl) | Cl | — | 0 |
| H | 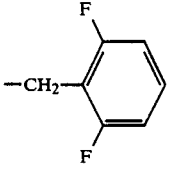 -CH₂-(2,6-difluorophenyl) | Cl | — | 0 |
| H | 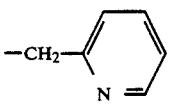 -CH₂-(2-pyridyl) | Cl | — | 0 |
| H | 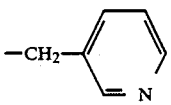 -CH₂-(3-pyridyl) | Cl | — | 0 |
| H | 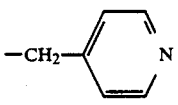 -CH₂-(4-pyridyl) | Cl | — | 0 |
| H | 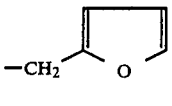 -CH₂-(2-furyl) | Cl | — | 0 |
| H | 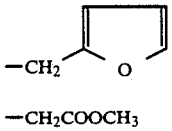 -CH₂-(2-furyl) | CF₃ | — | 0 |
| H | —CH₂COOCH₃ | Cl | — | 0 |
| H | —CH₂COOC₂H₅ | Cl | — | 0 |
| H | —CH(CH₃)—COOCH₃ | Cl | — | 0 |
| H | —CH(CH₃)—COOC₂H₅ | Cl | — | 0 |
| H | 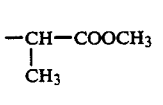 -CH₂-(4-methylphenyl) | Cl | — | 0 |
| H | 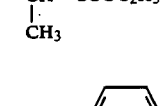 -CH₂-(4-methoxyphenyl) | Cl | — | 0 |
| H | —CH₂CH₂OH | Cl | — | 0 |
| —CH₂CH₂OH | —CH₂CH₂OH | Cl | — | 0 |
| H | —CH₂CH₂OCH₃ | Cl | — | 0 |
| —CH₂CH₂OCH₃ | —CH₂CH₂OCH₃ | Cl | — | 0 |

TABLE 1-continued
Examples of the compounds of the formula (I)
| R¹ | R² | R³ | R⁴ | n |
|----|----|----|----|---|
| H | 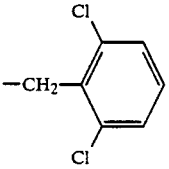 -CH₂-(2,6-dichlorophenyl) | Cl | — | 0 |
| H | —CH₂CH₂N(C₂H₅)₂ | Cl | — | 0 |
| H | 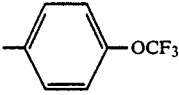 -C₆H₄-OCF₃ | Cl | — | 0 |
| H | -C₆H₄-SCF₃ | Cl | — | 0 |
| H | -C₆H₄-Br | Cl | — | 0 |
| H | 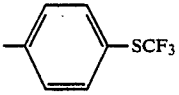 —CH₂CH₂-(2-methoxyphenyl) | Cl | — | 0 |
| H | 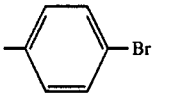 —CH₂CH₂-(4-methoxyphenyl) | Cl | — | 0 |
| H | 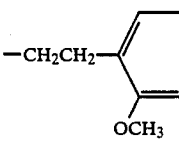 —CH₂CH₂-(3,4-dimethoxyphenyl) | Cl | — | 0 |
| H | 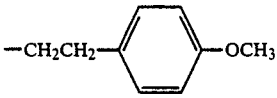 —CH₂CH₂CH₂—C₆H₅ | Cl | — | 0 |
| H | 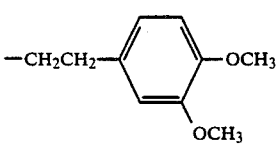 —CH₂CH₂-(3-methoxyphenyl) | Cl | — | 0 |
| H | —CH₂CH₂CH(C₆H₅)₂ | Cl | — | 0 |
| H | 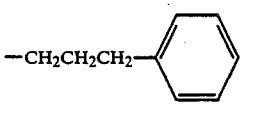 —CH₂-(4-tert-butylphenyl) | Cl | — | 0 |

TABLE 1-continued

Examples of the compounds of the formula (I)

| R¹ | R² | R³ | R⁴ | n |
|---|---|---|---|---|
| H | -CH₂-C₆H₄(OCH₃) (2-OCH₃ phenyl) | Cl | — | 0 |
| H | -CH₂-C₆H₃(OCH₃)₂ (3,4-dimethoxyphenyl) | Cl | — | 0 |
| H | -CH₂-C₆H₂(OCH₃)₃ (2,4,5-trimethoxyphenyl) | Cl | — | 0 |
| H | -CH₂-C₆H₄-CF₃ (4-CF₃ phenyl) | Cl | — | 0 |
| H | -CH₂-C₆H₅ | Cl | (5-)CF₃ | 1 |
| H | -CH₂-CH₂-N(pyrrolidinyl-2-CH₃) | Cl | — | 0 |

If, for example, 7-chloro-2-methylcarbamoylbenzothiazole 3-oxide and phosphoryl chloride are used as starting substances, the course of the reaction in the preparation process according to the invention can be represented by the following equation:

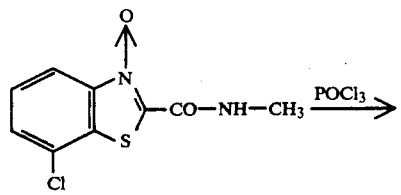
$\xrightarrow{POCl_3}$
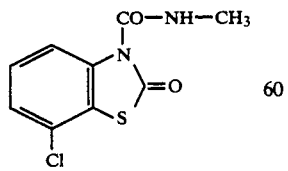

Formula (II) provides a general definition of the 2,7-disubstituted benzothiazole 3-oxides to be used as starting substances in the process according to the invention for the preparation of compounds of the formula (I).

In formula (II), n, R¹, R², R³ and R⁴ preferably, or in particular, have those meanings which have already been preferably described above, or described above as particularly preferred, for n, R¹, R², R³ and R⁴ in connection with the description of the compounds of the formula (I) according to the invention.

Examples of the starting substances of the formula (II) are listed in Table 2 below.

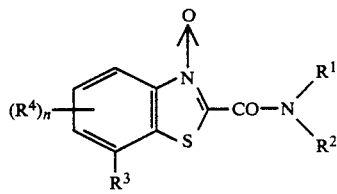

(II)

TABLE 2
Examples of the compounds of the formula (II)
| R¹ | R² | R³ | R⁴ | n |
|---|---|---|---|---|
| H | CH₃ | Cl | — | 0 |
| CH₃ | CH₃ | Cl | — | 0 |
| H | C₂H₅ | Cl | — | 0 |
| C₂H₅ | C₂H₅ | Cl | — | 0 |
| H | C₃H₇-n | Cl | — | 0 |
| H | CH(CH₃)₂ | Cl | — | 0 |
| H | C₄H₉-n | Cl | — | 0 |
| H | CH₂CH(CH₃)₂ | Cl | — | 0 |
| H | CH(C₂H₅)₂ | Cl | — | 0 |
| H | OH | Cl | — | 0 |
| H |  | Cl | — | 0 |
| H | 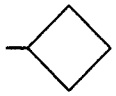 | Cl | — | 0 |
| H |  | Cl | — | 0 |
| H | 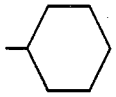 | Cl | — | 0 |
| H | —CH₂—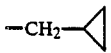 | Cl | — | 0 |
| H | —CH₂—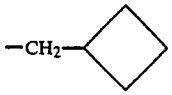 | Cl | — | 0 |
| H | —CH₂—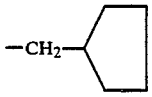 | Cl | — | 0 |
| H | —CH₂—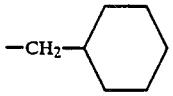 | Cl | — | 0 |
| H | —CH₂—CH=CH₂ | Cl | — | 0 |
| H | —CH₂—C≡CH | Cl | — | 0 |
| H | OCH₃ | Cl | — | 0 |
| H | OC₂H₅ | Cl | — | 0 |
| H | OC₃H₇-n | Cl | — | 0 |
| H | OCH(CH₃)₂ | Cl | — | 0 |
| H | OC₄H₉-n | Cl | — | 0 |
| H | OCH₂CH(CH₃)₂ | Cl | — | 0 |
| H | OCH₂CH=CH₂ | Cl | — | 0 |
| H | OCH₂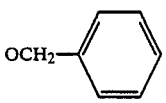 | Cl | — | 0 |
| H | —CH₂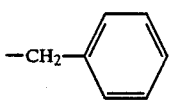 | Cl | — | 0 |

TABLE 2-continued
Examples of the compounds of the formula (II)
| R¹ | R² | R³ | R⁴ | n |
|---|---|---|---|---|
| CH₃ | 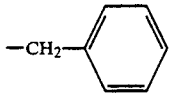 | Cl | — | 0 |
| H | 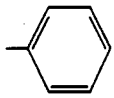 | Cl | — | 0 |
| H | 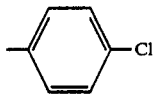 | Cl | — | 0 |
| H | 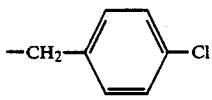 | Cl | — | 0 |
| H | 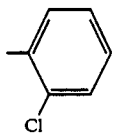 | Cl | — | 0 |
| H | 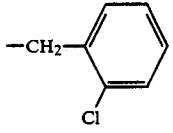 | Cl | — | 0 |
|  | —(CH₂)₄— | Cl | — | 0 |
|  | —(CH₂)₅— | Cl | — | 0 |
| H | 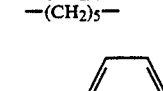 | Cl | (6-)Cl | 1 |
| H | 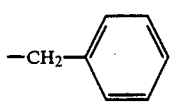 | Cl | — | 0 |
| H | 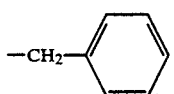 | Cl | — | 0 |
| H | 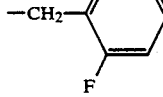 | Cl | — | 0 |
| H | 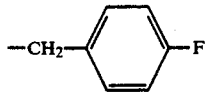 | Cl | — | 0 |

TABLE 2-continued

Examples of the compounds of the formula (II)

| R¹ | R² | R³ | R⁴ | n |
|---|---|---|---|---|
| H | —CH₂-(2-pyridyl) 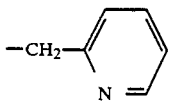 | Cl | — | 0 |
| H | —CH₂-(3-pyridyl) 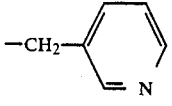 | Cl | — | 0 |
| H | —CH₂-(4-pyridyl) 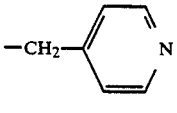 | Cl | — | 0 |
| H | —CH₂-(2-furyl) 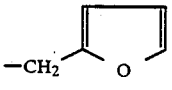 | Cl | — | 0 |
| H | —CH₂-(2-furyl) 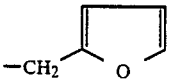 | CF₃ | — | 0 |
| H | —CH₂COOCH₃ | Cl | — | 0 |
| H | —CH₂COOC₂H₅ | Cl | — | 0 |
| H | —CH(CH₃)—COOCH₃ | Cl | — | 0 |
| H | —CH(CH₃)—COOC₂H₅ | Cl | — | 0 |
| H | —CH₂-C₆H₄-CH₃ 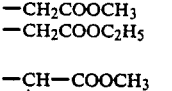 | Cl | — | 0 |
| H | —CH₂-C₆H₄-OCH₃ 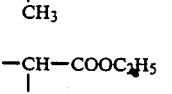 | Cl | — | 0 |
| H | —CH₂CH₂OH | Cl | — | 0 |
| —CH₂CH₂OH | —CH₂CH₂OH | Cl | — | 0 |
| H | —CH₂CH₂OCH₃ | Cl | — | 0 |
| —CH₂CH₂OCH₃ | —CH₂CH₂OCH₃ | Cl | — | 0 |
| H | —CH₂-(2,6-dichlorophenyl) 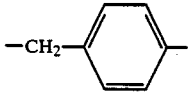 | Cl | — | 0 |
| H | —CH₂CH₂N(C₂H₅)₂ | Cl | — | 0 |
| H | -C₆H₄-OCF₃ 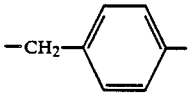 | Cl | — | 0 |
| H | -C₆H₄-SCF₃ 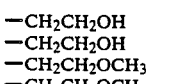 | Cl | — | 0 |

TABLE 2-continued

| R¹ | R² | R³ | R⁴ | n |
|---|---|---|---|---|
| H | —C₆H₄—Br (4-bromophenyl) | Cl | — | 0 |
| H | —CH₂CH₂—C₆H₄(2-OCH₃) | Cl | — | 0 |
| H | —CH₂CH₂—C₆H₄(4-OCH₃) | Cl | — | 0 |
| H | —CH₂CH₂—C₆H₃(3-OCH₃)(4-OCH₃) | Cl | — | 0 |
| H | —CH₂CH₂CH₂—C₆H₅ | Cl | — | 0 |
| H | —CH₂CH₂—C₆H₄(3-OCH₃) | Cl | — | 0 |
| H | —CH₂CH₂CH(C₆H₅)₂ | Cl | — | 0 |
| H | —CH₂—C₆H₄—C(CH₃)₃ (4-tert-butyl) | Cl | — | 0 |
| H | —CH₂—C₆H₄(3-OCH₃) | Cl | — | 0 |
| H | —CH₂—C₆H₃(3-OCH₃)(4-OCH₃) | Cl | — | 0 |
| H | —CH₂—C₆H₂(2-OCH₃)(3-OCH₃)(4-OCH₃) | Cl | — | 0 |

TABLE 2-continued

Examples of the compounds of the formula (II)

| R¹ | R² | R³ | R⁴ | n |
|---|---|---|---|---|
| H | −CH₂−C₆H₄−CF₃ | Cl | — | 0 |
| H | −CH₂−C₆H₅ | Cl | (5-)CF₃ | 1 |
| H | −CH₂−CH₂−N(pyrrolidinyl-2-CH₃) | Cl | — | 0 |
| CH₃ | −CH₂−C₆H₅ | Cl | — | 0 |
| H | −CH(CH₃)CH₂CH₃ | Cl | — | 0 |
| H | −CH₂CH₂−O−CH₂CH₂− | Cl | — | 0 |
| H | −CH₂C(CH₃)₃ | Cl | — | 0 |
| H | −CH₂−C₆H₄−OCH₃ | Cl | — | 0 |
| H | −CH(CH₃)−C₆H₅ | Cl | — | 0 |
| H | −CH₂CH₂−C₆H₅ | Cl | — | 0 |
| H | −CH₂−(naphthyl) | Cl | — | 0 |
| H | −CH₂−CH(OH)−C₆H₅ | Cl | — | 0 |
| H | −CH₂−(3,4-methylenedioxyphenyl) | Cl | — | 0 |

TABLE 2-continued
Examples of the compounds of the formula (II)
| R¹ | R² | R³ | R⁴ | n |
|---|---|---|---|---|
| H | 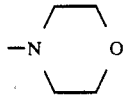 —N(CH₂CH₂)₂O (morpholino) | Cl | — | 0 |
| H | —CH₂CH₂CH₂—N(CH₂CH₂)₂O 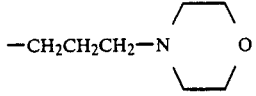 | Cl | — | 0 |
| H | —CH₂CHCH₃<br>      \|<br>     OH | Cl | — | 0 |
| H | —CH₂—C₆H₄—CF₃ 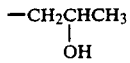 | Cl | (6-)Cl | 1 |
| H | —CH₂—(3,5-(CH₃)₂C₆H₃) 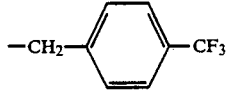 | Cl | — | 0 |
| H | —CH₂CH₂—C₆H₄—OCH₃ 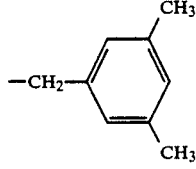 | Cl | — | 0 |
| H | —CH₂CH₂—C₆H₄—CF₃ 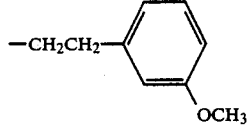 | Cl | — | 0 |
| H | —CH₂—C₆H₄—Cl 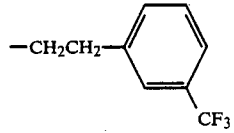 | Cl | — | 0 |
| H | —CH₂—C₆H₅ 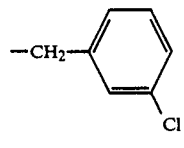 | CF₃ | — | 0 |
| H | —CH₂—(2,6-Cl₂-4-CF₃-C₆H₂) 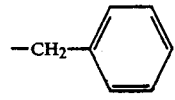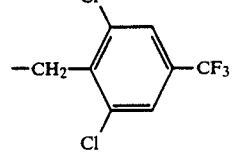 | Cl | — | 0 |
| H | —CH₂CH₂—C₆H₄—F 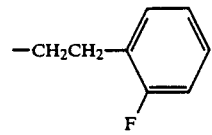 | Cl | — | 0 |

TABLE 2-continued

| R¹ | R² (Examples of the compounds of the formula (II)) | R³ | R⁴ | n |
|---|---|---|---|---|
| H | —CH₂CH₂—C₆H₃(F)(F) (2,4-difluorophenyl) | Cl | — | 0 |
| H | —CH₂CH₂—C₆H₄(CF₃) (2-CF₃-phenyl) | Cl | — | 0 |
| H | —CH₂CH₂—C₆H₄—CF₃ (4-CF₃-phenyl) | Cl | — | 0 |
| H | —CH₂CH₂—C₆H₄—F (3-F-phenyl) | Cl | — | 0 |
| H | —CH₂CH₂N(CH₃)₂ | Cl | — | 0 |
|   | —CH₂CH(CH₃)—O—CH(CH₃)—CH₂— | Cl | — | 0 |
| H | —CH₂—(N-ethylpyrrolidin-2-yl) | Cl | — | 0 |
| H | —CH₂CH₂CH₂—C₆H₅ | Cl | — | 0 |
| H | —CH(COOC₂H₅)—CH₂—C₆H₅ | Cl | — | 0 |

The starting substances of the formula (II) are the subject matter of Application Serial No. P 38 35 660.0 filed Oct. 20, 1988 in Germany, now pending.

The 2,7-disubstituted benzothiazole 3-oxides of the general formula (II) are obtained when 7-substituted 2-alkoxy-carbonyl-benzothiazole 3-oxides of the general formula (III)

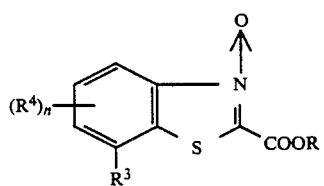

(III)

in which
n, R³ and R⁴ have the abovementioned meanings and R stands for alkyl, preferably having 1 to 4 carbon atoms,
are reacted with amines of the general formula (IV)

(IV)

in which
R¹ and R² have the abovementioned meanings,
if appropriate in the presence of diluents, such as, for example, methanol or ethanol, at temperatures of between 0° C. and 100° C.

The 7-substituted 2-alkoxycarbonyl-benzothiazole 3-oxides of the general formula (III) are likewise the subject matter of patent Application Serial No. P38 35 660.0 filed Oct. 20, 1988 in Germany, supra.

The 7-substituted 2-alkoxycarbonyl-benzothiazole 3-oxides of the general formula (III) are obtained when 2-chloro-nitrobenzene derivatives of the general formula (V)

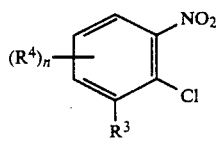 (V)

in which
n, $R^3$ and $R^4$ have the abovementioned meanings,
are reacted with mercaptoacetic acid esters of the general formula (VI)

HS—CH$_2$—COOR    (VI)

in which
R has the abovementioned meaning,
in the presence of a base, such as, for example, triethylamine, and in the presence of a diluent, such as, for example, dimethyl sulphoxide, benzene, toluene, tetrahydrofuran, dioxane, methanol, ethanol, propanol, isopropanol and/or water, at temperatures of between 0° C. and 100° C., preferably between 20° C. and 80° C.

The starting substances of the formulae (IV), (V) and (VI) are known chemicals for organic synthesis.

The process according to the invention for the preparation of the new compounds of the formula (I) is preferably carried out using diluents. Suitable diluents in this process are virtually all inert organic solvents. These include preferably aliphatic and aromatic, optionally halogenated hydrocarbons, such as pentane, hexane, heptane, cyclohex-ane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate, ethyl acetate, nitriles, such as, for example, acetonitrile and propionitrile, amides, such as, for example, dimethylformamide, dimethylacetamide and N-methylpyrrolidone, and also dimethyl sulphoxide, tetramethylenesulphone and hexamethylphosphoric triamide.

When carrying out the process according to the invention, the reaction temperatures may be varied within a relatively wide range. In general, the process is carried out at temperatures of between 0° C. and 150° C., preferably at temperatures of between 20° C. and 100° C.

In general, the process according to the invention is carried out under atmospheric pressure.

For carrying out the process according to the invention, the starting substances required in each case are generally employed in approximately equimolar amounts. However, it is also possible to use one of the two components employed in each case in excess. The reactions are generally carried out in a suitable diluent and the reaction mixture is stirred for several hours at the specific temperature required. In the process according to the invention, working up is carried out by the particular methods required.

The active compounds according to the invention exhibit a powerful biological action and can be employed in practice for combating undesired pests. For example, the active compounds are suitable for the use as plant protection agents, above all for combating fungi.

Fungicidal agents in plant protection are employed for combating plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some causative organisms of fungal diseases which come under the generic names listed above may be mentioned as examples, but not by way of limitation: Xanthomonas species, such as, for example, *Xanthomonas campestris* pv. oryzae; Pseudomonas species, such as, for example, *Pseudomonas syringae* pv. Lachrymans; Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septeoria species such as for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocerco sporella* herpotrichoides.

The good toleration, by plants, of the active compounds, at the concentrations required for combating plant diseases, permits treatment of above-ground parts of plants, of vegetative propagation stock and seeds, and of the soil.

The compounds of the formula (I) according to the invention show, in particular, a powerful protective action against Pyricularia species, such as, for example, *Pyricularia oryzae,* which cause damage in rice growing.

A good action against Phytophtora species is also observed.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussion Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and other growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

For the treatment of parts of plants, the active compound concentrations in the use forms can be varied within a substantial range. They are, in general, between 1 and 0.0001% by weight, preferably between 0.5 and 0.001%.

For the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

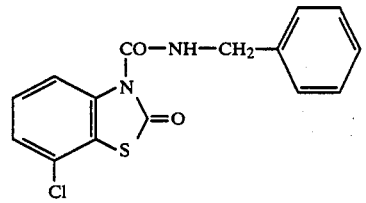

A mixture of 29.0 g (0.09 mole) of 7-chloro-2-benzylaminocarbonyl-benzothiazole 3-oxide and 150 ml of toluene is heated at 90° C., 13.8 g (0.09 mole) of phosphoryl chloride (phosphorus oxychoride, POCl$_3$) are added dropwise to the mixture, and the reaction mixture is stirred at 90° C. for 3 hours.

When the reaction mixture has cooled down, the 7-chloro-2-benzothiazolone crystals, which have been formed as the product of a side reaction, are filtered off with suction and the solvent is distilled off the filtrate under a water pump vacuum. The residue is chromatographed over a silica gel column, using chloroform as the solvent. 19.0 g (66% of theory) of 7-chloro-3-benzylaminocarbonyl-2-benzothiazolone of melting point 106° C. are obtained.

The compounds of the formula (I) listed in Table 3 below can be prepared in analogy to Example 1.

TABLE 3
Preparation Examples of the compounds of the formula (I)
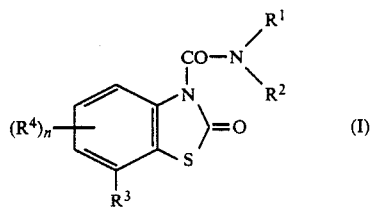
| Example No. | R¹ | R² | R³ | R⁴ | n | Physical data [Melting point °C.] |
|---|---|---|---|---|---|---|
| 2 | H | CH₃ | Cl | — | 0 | 128 |
| 3 | H | CH(CH₃)₂ | Cl | — | 0 | 92 |
| 4 | H | —CH₂—(3,4-methylenedioxyphenyl) | Cl | — | 0 | 140 |
| 5 | —CH₂CH₂—O—CH₂CH₂— | | Cl | — | 0 | 148 |
| 6 | H | CH₂CH(CH₃)₂ | Cl | — | 0 | 90 |
| 7 | H | —CH₂—(4-Cl-phenyl) | Cl | — | 0 | 156 |
| 8 | H | —CH₂—(2-Cl-phenyl) | Cl | — | 0 | 161 |
| 9 | H | —CH₂—phenyl | CF₃ | — | 0 | 110 |
| 10 | H | cyclohexyl | Cl | — | 0 | 108 |
| 11 | H | —CH₂—CH₂—(2-F-phenyl) | Cl | — | 0 | 121 |
| 12 | H | —CH₂—CH₂—(2,4-diF-phenyl) | Cl | — | 0 | 146 |
| 13 | H | —CH₂—CH₂—(2-CF₃-phenyl) | Cl | — | 0 | 119 |

TABLE 3-continued
Preparation Examples of the compounds of the formula (I)
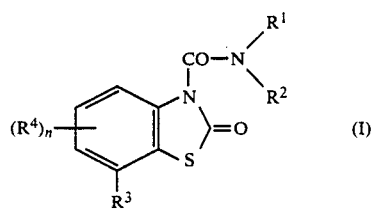
| Example No. | R¹ | R² | R³ | R⁴ | n | Physical data [Melting point °C.] |
|---|---|---|---|---|---|---|
| 14 | H | -CH₂-CH₂-C₆H₄(m-CF₃) | Cl | — | 0 | 119 |
| 15 | H | -CH₂-CH₂-C₆H₄(p-CF₃) | Cl | — | 0 | 125 |
| 16 | H | -CH₂-C₆H₄(p-F) | Cl | — | 0 | 163 |
| 17 | H | -CH₂-CH₂-C₆H₄(m-F) | Cl | — | 0 | 113 |
| 18 | H | -CH₂-C(CH₃)₃ | Cl | — | 0 | 74 |
| 19 | H | -CH₂-CH₂-C₆H₃(OCH₃)₂ | Cl | — | 0 | 129 |
| 20 | H | -CH₂-CH₂-C₆H₅ | Cl | — | 0 | 101 |
| 21 | H | -CH₂-C₆H₃(2,6-F₂) | Cl | — | 0 | 141 |
| 22 | H | -CH₂COOC₂H₅ | Cl | — | 0 | 119 |
| 23 | H | -CH₂-CH₂-CH₂-C₆H₅ | Cl | — | 0 | 66 |
| 24 | H | C₃H₇-n | Cl | — | 0 | 65 |
| 25 | H | -CH₂-CH=CH₂ | Cl | — | 0 | 95 |

TABLE 3-continued

Preparation Examples of the compounds of the formula (I)

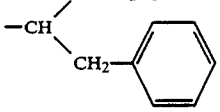

| Example No. | R¹ | R² | R³ | R⁴ | n | Physical data [Melting point °C.] |
|---|---|---|---|---|---|---|
| 26 | H | −CH(COOC$_2$H$_5$)(CH$_2$−C$_6$H$_5$) | Cl | — | 0 | 79 |
| 27 | H | −C$_6$H$_5$ | Cl | — | 0 | 143 |
| 28 | H | C$_2$H$_5$ | Cl | — | 0 | 82 |
| 29 | H | C$_4$H$_9$ | Cl | — | 0 | 66 |
| 30 | H | −CH$_2$−CH$_2$−(3-OCH$_3$-C$_6$H$_4$) | Cl | — | 0 | 111 |
| 31 | H | −CH(CH$_3$)−CH$_2$−CH$_3$ | Cl | — | 0 | (oil) |
| 32 | H | −CH$_2$−CN | Cl | — | 0 | 158 |
| 33 | H | CH$_3$ | CF$_3$ | — | 0 | 119 |
| 34 | H | −(4-Cl-C$_6$H$_4$) | Cl | — | 0 | 171 |
| 35 | H | −CH$_2$−CH$_2$−(3-F-C$_6$H$_4$) | CF$_3$ | — | 0 | 103 |
| 36 | H | −CH(CH$_3$)−COOC$_2$H$_5$ | Cl | — | 0 | 58 |
| 37 | H | −CH$_2$−CH$_2$−CN | Cl | — | 0 | 163 |
| 38 | H | −CH(CH(CH$_3$)$_2$)−COOCH$_3$ | Cl | — | 0 | (Oil) |
| 39 | H | −CH$_2$−(3-pyridyl) | Cl | — | 0 | 121 |
| 40 | H | −CH(CH(CH$_3$)$_2$)−COOC$_2$H$_5$ | Cl | — | 0 | (Oil) |

TABLE 3-continued
Preparation Examples of the compounds of the formula (I)
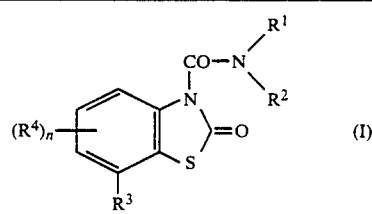
| Example No. | R¹ | R² | R³ | R⁴ | n | Physical data [Melting point °C.] |
|---|---|---|---|---|---|---|
| 41 | H | −CH₂−CH₂−(2-OCH₃-C₆H₄) | Cl | — | 0 | 117 |
| 42 | H | −CH₂−(3-OCH₃-C₆H₄) | Cl | — | 0 | 110 |
| 43 | H | −CH₂−(4-OCH₃-C₆H₄) | Cl | — | 0 | 119 |
| 44 | H | −CH₂−CH₂−(3-OCH₃-C₆H₄) | CF₃ | — | 0 | 112 |
| 45 | H | −CH₂−CH(OH)−C₆H₅ | Cl | — | 0 | 191 |
| 46 | H | −CH₂−CH₂−CH(CH₃)₂ | Cl | — | 0 | 92 |
| 47 | H | −CH₂−CH₂−C₆H₅ | CF₃ | (5-)Cl | 1 | 97 |
| 48 | H | −CH₂−C₆H₅ | CF₃ | (5-)Cl | 1 | 116 |
| 49 | H | −CH₂−CH₂−(3,4-(OCH₃)₂-C₆H₃) | CF₃ | (5-)Cl | 1 | 97 |
| 50 | H | −CH₂−C₆H₅ | Cl | (6-)Cl | 1 | 122 |

TABLE 3-continued

Preparation Examples of the compounds of the formula (I)

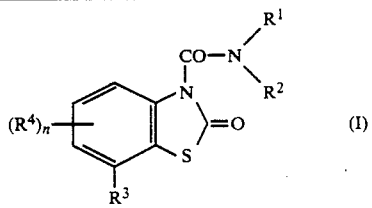

| Example No. | R¹ | R² | R³ | R⁴ | n | Physical data [Melting point °C.] |
|---|---|---|---|---|---|---|
| 51 | H | —CH₂—CH₂—C₆H₅ | Cl | (6-)Cl | 1 | 138 |
| 52 | H | —CH₂—C(CH₃)₃ | Cl | (6-)Cl | 1 | 125 |
| 53 | H | —CH₂—CO—C₆H₅ | Cl | — | 0 | 153 |

STARTING SUBSTANCES OF THE FORMULA (II)

Example (III-1)

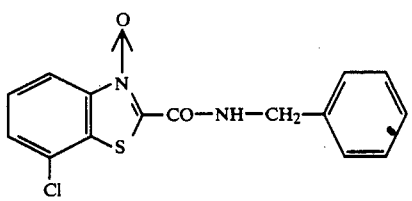

30.0 g (0.028 mole) of benzylamine are added dropwise and with stirring to a mixture of 6.1 g (0.025 mole) of 7-chloro-2-methoxy-carbonyl-benzothiazole 3-oxide and 100 ml of methanol, and the reaction mixture is stirred at 20° C. for 2 hours. The product obtained in this reaction has the form of crystals and is isolated by filtering off with suction.

7.5 g (94% of theory) of 7-chloro-2-benzylaminocarbonyl-benzothiazole 3-oxide of melting point 126° C. are obtained.

STARTING SUBSTANCES OF THE FORMULA (III)

Example (III-1)

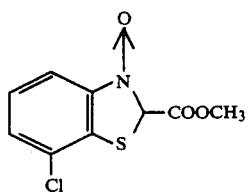

66 g (0.65 mole) of triethylamine are added dropwise and with stirring to a mixture of 115 g (0.60 mole) of 2,3-dichloronitrobenzene, 63.6 g (0.60 mole) of methyl mercaptoacetate and 250 ml of dimethyl sulphoxide. In this reaction, the internal temperature is maintained at 40° C. to 50° C. by external cooling When the addition of amine is complete, the reaction mixture is stirred for a further 12 hours at 20° C. The mixture is then diluted with methanol, and the product which is obtained in the form of crystals is isolated by filtering off with suction.

108 g (73% of theory) of 7-chloro-2-methoxy-carbonyl-benzothiazole 3-oxide of melting point 159° C. are obtained.

USE EXAMPLE

In the following use example, the compound shown below has been employed as comparison substance:

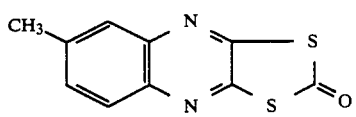

6-Methyl-2,3-quinoxalinedithiol cyclocarbonate (chinomethionate) (cf. DE-AS (German Published Specification) 1,100,372).

Example A

Pyricularia test (rice)/protective
Solvent: 12,5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, for example the compounds of preparation Examples (1), (2), (4), (6), (7), (11), (15) and (17) have a clearly superior activity compared with the prior art.

It will be appreciated that the instant specification and claims are set forth by way of illustration and not limitation, and that various modifications and changes may be made without departing from the spirit and scope of the present invention.

What is claimed is:

1. A disubstituted benzothiazolone of the formula

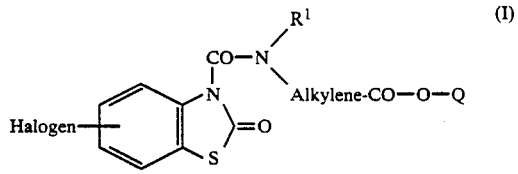

in which
$R^1$ is hydrogen or alkyl, and
Q is a hydrocarbyl radical.

2. A disubstituted benzothiazolone according to claim 1, in which
$R^1$ is hydrogen or $C_1$–$C_4$-alkyl,
Q is $C_1$–$C_4$-alkyl,
Alkylene has from 1 to 4 carbon atoms, and
Halogen is in the 7-position.

3. A compound according to claim 1, wherein such compound is 7-chloro-3-N-(ethoxycarbonylmethyl)-aminocarbonyl-2-benzothiazolone of the formula

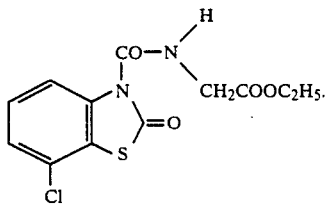

4. A fungicidal composition comprising a fungicidally effective amount of a compound according to claim 1 and a diluent.

5. A method of combating fungi which comprises applying to such fungi or to a fungus habitat a fungicidally effective amount of a compound according to claim 1.

6. The method according to claim 5, wherein such compound is
7-chloro-3-N-(ethoxycarbonylmethyl)-aminocarbonyl-2-benzothiazolone, or
7-chloro-3-N-(3,4-methylenedioxyphenylmethyl)-aminocarbonyl-2-benzothiazolone.

* * * * *